United States Patent [19]

Emmett et al.

[11] Patent Number: 4,556,711

[45] Date of Patent: Dec. 3, 1985

[54] 5-(4-AMINO OR ACYLAMINOPHENYL)-2(1H)-PYRAZINONES HAVING INOTROPIC ACTIVITY

[75] Inventors: John C. Emmett, Welwyn; Robert A. Slater, Letchworth; Brian H. Warrington, Welwyn Garden, all of England

[73] Assignee: Smith Kline & French Laboratories Ltd., Philadelphia, Pa.

[21] Appl. No.: 500,486

[22] Filed: Jun. 2, 1983

[30] Foreign Application Priority Data

Jun. 5, 1982 [GB] United Kingdom ............... 8216437
Jan. 8, 1983 [GB] United Kingdom ............... 8300476

[51] Int. Cl.$^4$ .................. C07D 241/18; C07D 403/12; C07D 413/12; C07D 401/12
[52] U.S. Cl. .................................. 544/357; 544/120; 544/405; 544/408
[58] Field of Search ................ 544/405, 408, 357, 120

[56] References Cited

U.S. PATENT DOCUMENTS 3,745,161 7/1973 Tsung-Ying et al. ............... 544/406

OTHER PUBLICATIONS

Greene ed., *Protective Groups in Organic Synthesis*, John Wiley & Sons, N.Y. (1981), pp. 222–249.
McOmie ed., *Protective Groups in Organic Chemistry*, Plenum Press, N.Y. (1973) pp. 46–61.
Sheradsky et al., J.C.S. Perkin I:1296–1299 (1977).
Ohta et al., Hukusokan Kagaku Toronkai Kuen Yoshishu 8th:84–88 (1975) (Chem. Abstr. 84:164,723Y).

*Primary Examiner*—Donald G. Daus
*Assistant Examiner*—William A. Teoli, Jr.
*Attorney, Agent, or Firm*—Edward T. Lentz; Janice E. Williams; Alan D. Lourie

[57] ABSTRACT

This invention relates to 5-(phenyl)-2(1H)-pyrazinones substituted in the 4-position of the phenyl ring by an amino or acylamino group. These compounds have inotropic activity. One specific compound is 5-(4-acetamidophenyl)-2(1H)-pyrazinone.

10 Claims, No Drawings

5-(4-AMINO OR ACYLAMINOPHENYL)-2(1H)-PYRAZINONES HAVING INOTROPIC ACTIVITY

The present invention relates to pyrazinone derivatives and in particular to such compounds having a substituted phenyl group at the 5-position of the pyrazinone ring. The invention further relates to processes for their preparation, their use as inotropic agents and to pharmaceutical compositions containing them.

The compound 5-(4-aminophenyl)pyrazin-2-one has been disclosed in the Journal of the Chemical Society, Perkin I, 1977, page 1296, but no useful biological activity was suggested.

Accordingly the present invention provides a pharmaceutical composition comprising a compound of the formula (I):

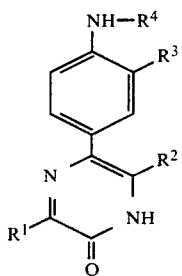
(I)

or a pharmaceutically acceptable salt thereof, wherein $R^1$, $R^2$ and $R^3$ are independently hydrogen or $C_{1-4}$-alkyl, and $R^4$ is hydrogen, or a $C_{1-6}$ alkoxycarbonyl group optionally substituted by amino, hydroxy, $C_{1-4}$-alkoxy or carboxy (wherein the substituent is not on the carbon atom adjacent to the —CO—O— moiety); or $R^4$ is a group —CO—$(NR^5)_n$—$R^6$ wherein n is zero or one, $R^6$ is hydrogen, optionally substituted $C_{1-6}$ alkyl, optionally substituted phenyl, or optionally substituted pyridyl, and $R^5$ is hydrogen or $C_{1-6}$ alkyl or $R^5$ and $R^6$ form together with the nitrogen atom to which they are attached a piperidine, morpholino, piperazine or N-($C_{1-6}$)alkylpiperazine ring; and a pharmaceutically acceptable carrier.

In one aspect of the invention $R^1$, $R^2$ and $R^3$ are as defined in relation to formula (I) and $R^4$ is hydrogen or a group —CO—$(NR^5)_n$—$R^6$ wherein n, $R^5$ and $R^6$ are as defined in relation to formula (I), with the proviso that when $R^5$ and $R^6$ form, together with the nitrogen atom to which they are attached, a ring system it is piperidino, piperazine or N-($C_{1-6}$)alkylpiperazine.

Suitably $R^1$ is $C_{1-4}$ alkyl for example methyl, ethyl, n-propyl or iso-propyl. Preferably $R^1$ is hydrogen.

Suitably $R^2$ is $C_{1-4}$ alkyl for example methyl. Preferably $R^2$ is hydrogen.

Suitably $R^3$ is $C_{1-4}$ alkyl for example methyl, ethyl, n-propyl or iso-propyl. Preferably $R^3$ is hydrogen.

Thus in a preferred aspect of the compounds of the formula (I), $R^1$, $R^2$ and $R^3$ are simultaneously hydrogen.

Preferably $R^4$ is a hydrogen atom.

Suitably $R^4$ is a $C_{1-6}$ alkoxycarbonyl group, for example methoxycarbonyl, ethoxycarbonyl or t-butoxycarbonyl. More suitably $R^4$ is methoxycarbonyl or ethoxycarbonyl, preferably methoxycarbonyl. In an alternative aspect $R^4$ is $C_{2-6}$ alkoxycarbonyl substituted by amino or hydroxy, for example 2-hydroxyethoxycarbonyl or 2-aminoethoxycarbonyl.

When $R^6$ is $C_{1-6}$ alkyl suitable optional substituents include up to three groups or atoms selected from carboxy, chloro, bromo, fluoro, amino, hydroxy, $C_{1-4}$ alkoxy, $C_{1-6}$ alkanoylamino, phenyl and phenyl substituted with amino, chloro, fluoro, bromo or $C_{1-4}$ alkyl.

When $R^6$ is optionally substituted phenyl suitable substituents include amino, chloro, fluoro, bromo or $C_{1-4}$ alkyl and $C_{1-4}$ alkoxy. When $R^6$ is optionally substituted pyridyl suitable substituents include amino, hydroxy, $C_{1-4}$ alkyl and $C_{1-4}$ alkoxy.

In one aspect $R^6$ is $C_{1-6}$ alkyl, $C_{1-6}$ alkyl substituted by carboxy, hydroxy, acetamido or halo such as chloro, phenyl, phenyl substituted by amino or is pyridyl.

In one aspect n is zero. When n is zero, favourably $R^4$—NH— is $C_{1-6}$ alkanoylamino, examples of which include acetamido, propionamido and butyramido, of these acetamido is particularly favoured. Suitably also $R^4$ is benzoyl, and in a further aspect $R^4$ is benzoyl substituted by amino, for example in the 3- or 4-position of the phenyl ring.

Preferably $R^4$ is hydrogen or acetyl.

Thus preferred compounds for use in the compositions of this invention are those of the formula (II):

(II)

and pharmaceutically acceptable salts thereof wherein $R^7$ is hydrogen or acetyl.

In another aspect n is one. In such compounds $R^5$ may be hydrogen or $C_{1-6}$ alkyl for example methyl, ethyl, n-propyl or isopropyl. $R^6$ may be hydrogen, $C_{1-6}$ alkyl such as methyl, ethyl, n-propyl or isopropyl, or $R^6$ may be $C_{1-6}$ alkyl substituted by carboxy such as carboxymethyl or carboxyethyl, $C_{1-6}$ alkyl substituted by hydroxy for example hydroxyethyl, or $C_{1-6}$ alkyl substituted by amino or $C_{1-6}$ alkanoylamino for example aminoethyl, aminopropyl, aminobutyl or acetamidoethyl. In another aspect $R^6$ may be $C_{1-6}$ alkyl substituted by carboxy and by amino such as 5-amino-5-carboxypentyl. Suitably in such compounds $R^6$ is hydrogen, $C_{1-6}$ alkyl such as methyl, ethyl, n-propyl or iso-propyl, benzyl or phenyl.

More suitably $R^5$ is hydrogen and $R^6$ is hydrogen, methyl, ethyl, propyl, butyl or phenyl.

More suitably $R^5$ and $R^6$ have the same value, for example —$NR^5R^6$ may be amino, dimethylamino or di-ethylamino.

In another aspect $R^5$ and $R^6$ are joined to form together with the nitrogen atom to which they are attached a piperidine, piperazine or N-($C_{1-6}$)alkylpiperazine ring such as N-methylpiperazine.

Thus in a preferred aspect compounds for use in the compositions of this invention when n is one include those of the formula (III):

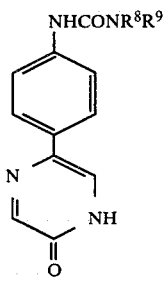

(III)

and pharmaceutically acceptable salts thereof wherein $R^8$ is hydrogen or $C_{1-6}$ alkyl and $R^9$ is hydrogen, $C_{1-6}$ alkyl such as methyl, ethyl, n-propyl, isopropyl, t-butyl, sec-butyl, n-butyl or isobutyl, benzyl or phenyl.

Formulae (I) to (III) are depicted as 2(1H)-pyrazinones, but of course the present invention covers all tautomeric forms thereof.

Compounds of the formulae (I) to (III) having a free amino group may form pharmaceutically acceptable acid addition salts with either organic or inorganic acids, for example those formed with hydrochloric, hydrobromic, hydriodic, methanesulphonic, sulphuric, maleic, fumaric, succinic, acetic, oxalic, tartaric, citric and lactic acids. The compounds of the formulae (I) and (II) may form salts with metal ions, such as alkali metals for example sodium and potassium, or alkaline earth metals for example calcium and magnesium. Any carboxy group present may be optionally salified. The ability to form acid addition and/or metal salts will be subject to the nature of the relevant compounds as will be readily understood by the skilled man.

In another aspect the present invention provides the compounds of the formula (I) and pharmaceutically acceptable salts thereof with the exception of 5-(4-aminophenyl)-2-(1H)-pyrazinone.

Suitable, favoured and preferable values for the groups $R^1$ to $R^9$ for these novel compounds are as previously disclosed in relation to the use of the compounds of the formula (I) in pharmaceutical compositions.

In order to use a compound of the formula (I) or a pharmaceutically acceptable salt thereof for the treatment of mammals including humans it is normally formulated in accordance with standard pharmaceutical practice as a pharmaceutical composition.

In a preferred composition aspect of this invention a compound of the formula (I) is in sterile form.

Compounds of formula (I) and their pharmaceutically acceptable salts may be administered orally, parenterally, trans-dermally or rectally.

Compounds of formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet or capsule, any pharmaceutical carrier routinely used for preparing solid formulations may be used. Examples of such carriers include magnesium stearate, starch, lactose and sucrose.

Typical parenteral compositions consist of a solution or suspension of the compound or salt in a sterile aqueous carrier or parenterally acceptable oil, for example polyethylene glycol in saline.

A typical suppository formulation comprises a compound of formula (I) or a pharmaceutically acceptable salt thereof which is active when administered in this way, with a binding and/or lubricating agent for example gelatin or cocoa-butter or other low melting vegetable waxes or fats.

Preferably the composition is in unit dosage form for example a tablet or capsule so that the patient may administer to himself a single dose.

Each dosage unit contains preferably from 15 to 250 mg of a compound of formula (I) or a pharmaceutically acceptable salt thereof calculated as the pyrazinone.

The daily dosage regimen for a mammal is from about 0.25 mg/Kg to about 25 mg/Kg of the compound of formula (I) or a pharmaceutically acceptable salt thereof calculated as the free pyrazinone moiety. The active ingredient may be administered from 1 to 6 times a day, sufficient to increase cardiac output. The compositions of the present invention have positive inotropic activity and vasodilator activity and are of use in the treatment of cardiovascular diseases which can be treated by compounds having either or both of these activities. One such disease condition is congestive heart failure.

The compounds of this invention may be co-administered with other pharmaceutically active compounds, such compounds employed in their usual effective dose range. Conveniently the compounds of this invention and the other active compound or compounds are formulated in a pharmaceutical compositions. Examples of compounds which may be included in pharmaceutical compositions with the compounds of the formula (I) are vasodilators for example hydralazine, renal vasodilators for example 6-chloro-7,8-dihydroxy-1-(4'-hydroxyphenyl)-2,3,4,5-tetrahydro-1H-3-benzazepine methanesulphonate, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, cardioglycosides for example digoxin and digitoxin, calcium antagonists for example verapamil and nifedipine, diuretics such as thiazides and related compounds for example benzdrofluazide, chlorothiazide, chlorothalidone, hydrochlorothiazide, and other diuretics for example frusemide and triamterene, and sedatives for example nitrazepam, flurazepam and diazepam.

The compounds of the formula (I) and pharmaceutically acceptable salts thereof may be prepared by a process which comprises:

(a) acylating a compound of the formula (I) as hereinbefore defined wherein $R^4$ is hydrogen or a derivative thereof that permits acylation to take place;

(b) to form a compound of the formula (I) wherein $R^5$ is hydrogen, reacting a compound of the formula (I) as hereinbefore defined wherein $R^4$ is hydrogen with an isocyanate;

(c) the reaction of a compound of the formula (IV):

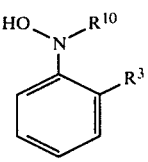

(IV)

wherein $R^3$ is as hereinbefore defined, and $R^{10}$ is a protecting group or a group $R^4$ as hereinbefore defined other than hydrogen, with a compound of the formula (V):

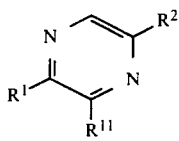
(V)

wherein $R^1$ and $R^2$ are as hereinbefore defined and $R^{11}$ is a leaving group; or (d) the reduction of a compound of the formula (VI):

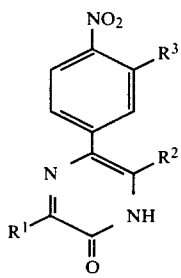
(VI)

wherein $R^1$, $R^2$ and $R^3$ are as hereinbefore defined; or (e) the reaction of a compound of the formula (VII):

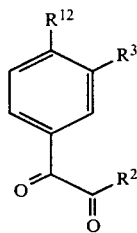
(VII)

wherein $R^2$ and $R^3$ are as hereinbefore defined and $R^{12}$ is nitro or a group $R^{10}$ wherein $R^{10}$ is a protecting group or a group $R^4$ other than hydrogen, with a compound of the formula (VIII):

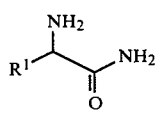
(VIII)

wherein $R^1$ is as hereinbefore defined, and if $R^{12}$ is nitro reducing to amino; or (f) to form a compound of the formula (I) wherein n is one, the reaction of a compound of formula (IX):

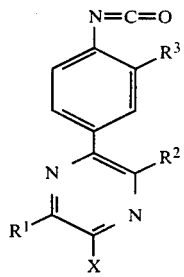
(IX)

wherein $R^1$, $R^2$ and $R^3$ are as hereinbefore defined and X is hydroxy or chloro, with an amine of the formula (X):

$$HNR^{5'}R^{6'} \qquad (X)$$

wherein $R^{5'}$ and $R^{6'}$ are groups $R^5$ and $R^6$ respectively as hereinbefore defined or are protected derivatives thereof, and if X is chloro hydrolysing to a compound wherein X is hydroxy:

and thereafter if necessary:
(i) removing any protecting group,
(ii) acylating the amino group ($R^4$) or derivative thereof that permits acylation to take place,
(iii) if it is desired to form compounds wherein $R^5$ is hydrogen, reacting the amino group ($R^4$) with an isocyanate,
(iv) forming a pharmaceutically acceptable salt.

Suitably $R^{11}$ is a leaving group such as a sulphonyloxy group for example mesylate or tosylate, a $C_{1-6}$ alkylthio group for example methylthio, a $C_{1-6}$ alkoxy group for example methoxy or halo for example bromo or chloro. Preferably $R^{11}$ is chloro. The reaction of a compound of the formula (IV) with a compound of the formula (V) is generally performed in the presence of a base for example an alkali metal hydroxide such as sodium hydroxide or potassium hydroxide in dimethylformamide (containing sufficient water to dissolve the hydroxide) or in a $C_{1-4}$ alkanol for example ethanol, a metal hydride such as sodium hydride in an aprotic organic solvent such as dimethylformamide, or an alkali metal carbonate such as potassium carbonate in acetone.

It is believed that the reaction of a compound of the formula (IV) and a compound of the formula (V) passes through the intermediate:

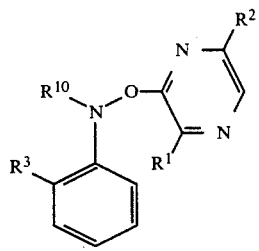

wherein $R^1$, $R^2$ and $R^3$ and $R^{10}$ are as hereinbefore defined.

When $R^{10}$ is a protecting group, suitably it is a group removable in conventional manner for example benzyloxycarbonyl or such a group optionally substituted such as p-nitrobenzyloxycarbonyl. Such groups are removable on treatment with inorganic acid, for example hydrogen bromide in acetic acid, or such groups may be removed on catalytic hydrogenation, for example using Palladium on Carbon.

Compounds of the formula (I) wherein $R^4$ is an acyl group (i.e. wherein $R^4$ is other than hydrogen) may be prepared from the compounds of the formula (I) wherein $R^4$ is hydrogen, or a derivative thereof that permits acylation to take place, via conventional methods of acylation. For example using an acid halide, an acid anhydride or an activated ester. An example of a class of derivatives of the amino group that permit acylation to take place is the silylated amines. Any amino group present as a substituent on $R^4$ may be protected in conventional manner during the acylation reaction.

The compound of formula (I) wherein $R^4$ is hydrogen may be reacted with an appropriate isocyanate to form a compound of the formula (I) wherein n is one and $R^5$ is hydrogen. The reaction is conveniently performed in an inert organic solvent such as dimethylformamide at an ambient or elevated temperature, for example at room temperature or a temperature up to about 100° C. Suitably the reaction is performed at room temperature for example 10°–30° C.

Suitably the reduction of a compound of the formula (VI) is performed via catalytic hydrogenation, either using hydrogen gas or via catalytic transfer hydrogenation, suitably in the presence of a base. Suitable catalysts include conventional transition metal catalysts for example Palladium on a conventional carrier, for example about 10% Palladium on Charcoal. The hydrogenation may be performed at non-extreme pressure, for example at atmospheric pressure or at pressures of up to 10 atmospheres ($10.13 \times 10^5$ Pa), preferably at about 3 atmospheres ($3 \times 10^5$ Pa). Suitably the base is in aqueous alcohol for example hydroxide in a $C_{1-4}$ alkanol for example ethanol. In an alternative aspect the reduction is performed with hydrazine as the hydrogen source in aqueous base in the presence of a conventional transition metal catalyst for example 10% Palladium on Charcoal preferably at an elevated temperature. In one aspect the aqueous base may be hydrazine, alternatively the aqueous base may be sodium hydroxide or the like.

The compounds of the formula (VI) may be prepared by the nitration of the compounds of the formula (XI):

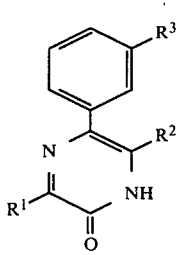

(XI)

wherein $R^1$, $R^2$ and $R^3$ are as hereinbefore defined.

The compounds of formula (IV), (V) and (XI) can be prepared by known methods.

Suitably the nitration of the compounds of the formula (XI) is performed at low temperatures for example below 5° C. and more suitably between $-5°$ C. and $-25°$ C., for example at about $-15°$ C. We have found a mixture of fuming nitric acid and sulphuric acid to be an effective nitrating agent, preferably in a ratio of between 4:1 to 8:1 (vol/vol), for example about 6:1. We have found that at ambient temperatures and at elevated temperatures (for example 50° C.) that a number of undesired reactions occur; that is to say the pyrazinone ring can cleave, and nitration can preferentially occur on the pyrazinone ring particularly when $R^1$ is hydrogen giving rise to undesirable mono- and di-nitration products. It has been reported (Chem. Abs. 84: 164723y) that the nitration of a compound of the formula (XI) wherein $R^1$, $R^2$ and $R^3$ are simultaneously hydrogen gives rise to a compound wherein a nitro group replaces $R^1$. This was unambiguously proved by an alternative synthesis. Thus it is unexpected that compounds of the formula (VI) are prepared in high yields (about 80%) by the nitration of compounds of the formula (XI).

In one aspect, provided $R^{10}$ is not a ureido group, we have found it convenient to generate the compounds of the formula (IV) from compounds of the formula (XII):

wherein $R^{10}$ and $R^3$ are as hereinbefore defined, and $R^{13}$ is a hydroxy protecting group such as $C_{1-6}$ alkanoyl for example acetyl. The compounds of the formula (IV) are formed via the reaction of a base such as hydroxide or alkoxide for example methoxide in an aqueous polar organic solvent for example aqueous dimethylformamide or aqueous dimethylsulphoxide. The compound of the formula (IV) may be isolated or may be reacted in situ with the compound of the formula (V).

In general the reaction between a compound of the formula (VII) and a compound of the formula (VIII) is performed under basic conditions, and conveniently is carried out in solution in an aqueous $C_{1-4}$ alkanol.

The reaction of a compound of the formula (IX) with a compound of the formula (X) is generally performed in an organic aprotic solvent for example dimethylformamide. The reaction is conveniently carried out at ambient temperature.

Suitably in the compounds of the formula (IX), X is hydroxy. If X is chloro then the compounds of the formula (I) may be prepared by hydrolysis, for example mild acid or base hydrolysis.

The compounds of the formula (IX) may be prepared by the reaction of a compound of the formula (XIII):

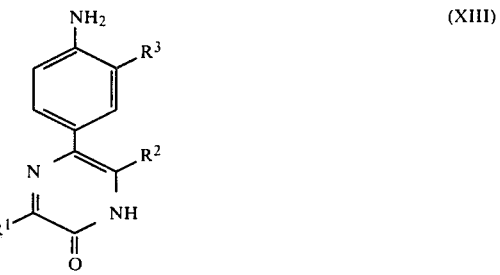

with a carbonylating agent, and if it is desired to prepare a compound of the formula (IX) wherein X is chloro, the carbonylating agent must also be a chlorinating agent. An example of a carbonylating agent is N,N′-carbonyldi-imidazole, and an example of a carbonylating agent that is also a chlorinating agent is phosgene. Such reagents are reacted with the amino compound of the formula (IX) in conventional manner, for example in an aprotic solvent such as dimethylformamide, at an ambient temperature or with cooling, for example about 0° C. The reaction is performed in the presence of an organic base, for example triethylamine.

Alternatively the compound of the formula (XIII) may be converted to the corresponding chloropyrazine with a chlorinating agent for example trichloromethyl chloroformate, and subsequently converted to a compound of the formula (IX) with a carbonylating agent.

In addition the compounds of the formula (IX) may be prepared by heating compounds of the formula (XIV):

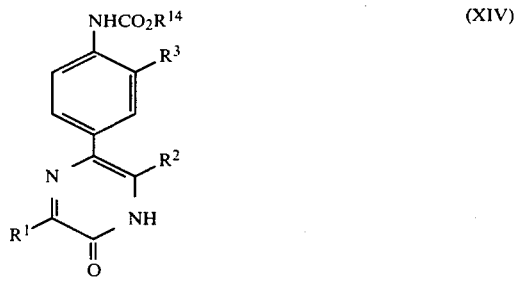

wherein $R^1$, $R^2$ and $R^3$ are as hereinbefore defined and $R^{14}$ is $C_{1-6}$ alkyl such as methyl and ethyl, aryl such as phenyl.

Pharmaceutically acceptable salts of the compounds of the formula (I) may be prepared in conventional manner, for example acid addition salts may be prepared by treating those compounds containing a basic group of the formula (I) with the appropriate acid in a $C_{1-4}$ alkanol, or they may be prepared by the use of an ion-exchange resin to form the desired salt directly from the free base or via a different acid addition salt.

Test Method

The activity of the compounds for use in this invention as cardiac stimulants, also known as cardiotonic agents, is demonstrated by a positive inotropic effect.

The compounds of formula (I) and their pharmaceutically acceptable salts are tested for cardiac stimulant activity following a procedure based on that of S. C. Verma and J. H. McNeill (J. Pharm & Exp. Therapeutics, 200, 352-362 (1977)). Guinea pigs (500-700 g) of either sex are sacrificed and the hearts are quickly removed and transferred to a dissecting dish containing oxygenated bathing fluid. While in the bathing medium, the right ventricle is cut into two strips. The strips are each suspended in a 75 ml bath containing Krebs Henseleit solution at 37° C., and the bath is bubbled with 95% oxygen and 5% carbon dioxide. The ventricular strips are electrically stimulated at a frequency of 0.5 Hz, at double the threshold voltage. A resting tension of 1.0 g is applied to the strips and the tension is kept constant by readjustment during an equilibration period of 60 minutes. The bathing fluid is frequently changed during this period. When a steady base line is obtained, a compound under test is added to the bathing fluid and a cumulative concentration response curve is plotted. The compounds for use in the present invention which were tested resulted in a 50% increase in the force of contraction of the ventricular strips at concentrations in the bathing fluid of less than $10^{-4}$ molar, thus showing that they have activity as positive inotropic agents. The compounds of the Examples gave the following data when subjected to the above test method. The compounds of Examples 3, 10, 16, 17 and 19 gave $EC_{50}$ values of below 10 $\mu$M. The compounds of Examples 2, 4, 5, 14 and 18 gave $EC_{50}$ values of between 10 and 100 $\mu$M.

5(4-Acetamidophenyl)-2(1H)-pyrazinone has been shown when administered intravenously in 20% polyethylene glycol solution to conscious dogs, to increase left ventricular dp/dt max by at least 50% at dosage levels below 1 mg/Kg. There was no statistically significant change in blood pressure or heart rate.

The compounds for use in this invention show no overt signs of toxicity at doses which are a multiple of the therapeutic doses.

The following Description and Examples serve to illustrate the invention.

DESCRIPTION 1

5-(4-Benzyloxycarbonylaminophenyl)-2(1H)-pyrazinone

A solution of benzyl N-hydroxy-N-phenylcarbamate (8.0 g) in ethanolic potassium hydroxide (0.27N; 120 ml) was treated with chloropyrazine (4.18 g) and molecular sieve (0.5 g). The mixture was stirred for 2 hours at room temperature and then allowed to stand for 4 days. Evaporation of the reaction mixture under reduced pressure gave an orange residue which was suspended in dilute acetic acid, filtered off, and heated in hot 1-propanol (about 200 ml). On cooling, the resulting solution gave a golden precipitate of 5-(4-benzyloxycarbonylaminophenyl)-2(1H)-pyrazinone m.p. 240°-4° C.

EXAMPLE 1

5-(4-Aminophenyl)-3-methyl-2(1H)-pyrazinone hydrobromide (a) To a stirred suspension of sodium hydride (2.1 g, 50% in oil) in dry dimethylformamide (35 ml) with external cooling was added portionwise, benzyl N-hydroxy-N-phenylcarbamate (10.6 g). After 5 minutes a brown solution was obtained to which was added 2-chloro-3-methylpyrazine (5.5 g) and the mixture was allowed to attain room temperature. The solution was poured into water (200 ml) and the aqueous phase decanted from the dark oil. The aqueous solution deposited a yellow solid which was collected and washed with ethanol to give 5-(4-benzyloxycarbonylaminophenyl)-3-methyl-2(1H)-pyrazinone (1.55 g. m.p. 238°-240° C.).

(b) 5-(4-Benzyloxycarbonylaminophenyl)-3-methyl-2(1H)pyrazinone (1.5 g) was treated with hydrogen bromide in acetic acid in a manner similar to that described in Example 20 to give the title compound as its hydrobromide salt (1.09 g) which on recrystallisation from ethanol/ether had m.p.>300° C.; $\nu$(Nujol mull) 1632, 1640 cm$^{-1}$.

EXAMPLE 2

5-(4-Aminophenyl)-6-methyl-2(1H)-pyrazinone hydrobromide (a) 2-Chloro-6-methylpyrazine (2.0 g) was treated with benzyl N-hydroxy-N-phenylcarbamate (3.7 g) in a manner similar to that described in Example 1(a) to give 5-(4-benzyloxycarbonylaminophenyl)-6-methyl-2(1H)-pyrazinone (0.52 g) which on recrystallisation from ethanol had m.p. 232° C.

(b) 5-(4-Benzyloxycarbonylaminophenyl)-6-methyl-2(1H)-pyrazinone (0.5 g) was treated with hydrogen bromide in acetic acid in a manner similar to that described in Example 20 to give the title compound as its hydrobromide salt (340 mg) which after digestion with hot ethanol had m.p.>300° C.; δ(D₂O) inter alia 2.39 (3H, d, CH₃), 8.03 (1H, q, pyrazinone ring 3-H); ν(KBr) 1705, 1750 cm⁻¹.

EXAMPLE 3

5-(4-Acetamidophenyl)-2(1H)-pyrazinone (a) 5-(4-Aminophenyl)-2(1H)-pyrazinone hydrobromide (2.5 g) in water (20 ml) was treated with acetic anhydride (1.2 g) and anhydrous sodium acetate (1.4 g). The mixture was stirred at room temperature for 1 hour, and the crude product (1.58 g; m.p. 268°-275° C.) was filtered off. This material was thoroughly washed with water and recrystallised from glacial acetic acid to give 5-(4-acetamidophenyl)-2(1H)-pyrazinone (0.84 g; m.p. 287°-8° C.).

(b) N-Acetylphenylhydroxylamine (100 g) and 2-chloropyrazine (79 g) were dissolved in anhydrous dimethylformamide (500 ml). Sodium hydride (50% oil; 46 g) was added in portions over 1½ hours, ensuring that the temperature was maintained between 20°-40° C. The reaction mixture was cooled, diluted with water (2500 ml); washed with dichloromethane (4 times) and filtered through diatomaceous earth. Acetic acid was slowly added with stirring to take the pH of the filtrate to 5-6. During this addition crystalline solid formed. After 30 minutes, this was collected by filtration, washed with very dilute acetic acid and dried at 60° C. to yield 5-(4-acetamidophenyl)-2-(1H)-pyrazinone (94.6 g).

(c) The process of Example 3b may be carried out using sodium hydroxide in dimethylformamide (containing sufficient water to dissolve the hydroxide) instead of sodium hydride. This afforded the title compound in 38% yield.

(d) The process of Example 3b was carried out using potassium carbonate in acetone. This afforded the title compound in 33% yield.

EXAMPLE 4

5-(4-Acetamidophenyl)-3-methyl-2(1H)-pyrazinone 5-(4-Aminophenyl)-3-methyl-2(1H)-pyrazinone hydrobromide (1.0 g) in water (25 ml) was treated with acetic anhydride and sodium acetate in a similar manner to that described in Example 3. On recrystallisation from aqueous acetic acid the title compound (0.68 g) had m.p.>300° C.; δ(DMSO-d₆) inter alia 2.08 (3H,s, CO—CH₃), 2.39 (3H, d, 3-CH₃), 10.0 (1H, s, NHCO); ν(Nujol mull) 1655 (C=O) cm⁻¹.

EXAMPLE 5

5-(4-Benzamidophenyl)-2(1H)-pyrazinone

A solution of 5-(4-aminophenyl)-2(1H)-pyrazinone hydrobromide (2.0 g) in aqueous sodium hydroxide (46 ml, 10%) was treated with benzoyl chloride (1.9 ml) and the mixture was agitated for 2 hours at room temperature. The pale yellow precipitate was collected, washed with water and dried. Recrystallisation from glacial acetic acid gave the title compound (0.9 g), m.p.>300° C.; ν(Nujol mull) 1660 (C=O), 1705 (C=O), 3330 (NH)cm⁻¹.

EXAMPLE 6

5-[4-(4-Aminobenzamido)phenyl]-2(1H)-pyrazinone (a) A solution of 5-(4-aminophenyl)-2(1H)-pyrazinone (1.7 g) in sodium hydroxide was reacted with 4-nitrobenzoyl chloride (1.8 g) in a manner similar to that described in Example 9 to give 5-[4-(4-nitrobenzamido)phenyl]-2(1H)-pyrazinone (1.5 g, m.p. 298°-300° C.).

(b) 5-[4-(4-Nitrobenzamido)phenyl]-2(1H)-pyrazinone (1.0 g) was added to a vigorously stirred suspension of palladium on charcoal (0.3 g, 5%) in ethanol (20 ml) followed by cyclohexene (20 ml). The reaction was heated under reflux for 24 hours, hot dimethylformamide was then added and the mixture was filtered. Evaporation of the filtrate gave a solid residue which was extracted with boiling glacial acetic acid, collected and dried to give the title compound (0.6 g, m.p. >300° C.; δ(DMSO-d₆) 7.99 and 8.09 (2H, 2s, pyrazinone ring protons), 9.7 and 9.9 (2H, 2 broad s, =CH—NH—CO and —NH—CO).

EXAMPLE 7

5-[4-(3-Aminobenzamido)phenyl]-2(1H)-pyrazinone (a) To a stirred solution at N-phenylhydroxylamine (6.5 g) in ether (65 ml) at 0° C. was added dropwise over 30 minutes a solution of 3-nitrobenzoyl chloride (5.5 g) in ether. Stirring was continued for 1 hour, the mixture allowed to stand at room temperature overnight then filtered. Evaporation of the filtrate left an oil which was dissolved in toluene, light petroleum was added and the mixture left overnight at 0° C. N-Hydroxy-N-(3-nitrobenzoyl)-N-phenylhydroxylamine separated as an oil (10 g) which was isolated by decantation for use in the next reaction.

(b) N-Hydroxy-N-(3-nitrobenzoyl)-N-phenylcarbamate was treated with 2-chloropyrazine and sodium hydride in a manner similar to that described in Example 1(a) to give 5-[4-(3-nitrobenzamido)phenyl]-2(1H)-pyrazinone, as a yellow solid, m.p.>250° C.

(c) 5-[4-(3-Nitrobenzamido)phenyl]-2(1H)-pyrazinone was reduced with cyclohexene and palladium on charcoal in ethanol in a manner similar to that described in Example 6 to give the title compound (60%) m.p.>250° C.; δ(DMSO-d₆) 8.01 and 8.10 (2H, ABq, pyrazinone ring protons),

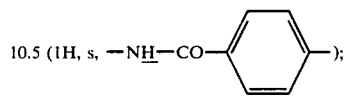

ν(Nujol mull) 1525 (—NHCO), 1660 (C=O) cm⁻¹.

EXAMPLE 8

5-[4-(5-Chloro-n-valeramido)phenyl]-2(1H)-pyrazinone

To a stirred suspension of 5-(4-aminophenyl)-2(1H)-pyrazinone hydrobromide (1.2 g) in toluene (30 ml) was added 5-chloro-n-valeryl chloride (0.57 g). The mixture was heated under reflux for 10 hours then evaporated to small volume and toluene (10 ml) was added to the residue. The resultant brown solid (0.7 g) was recrystallised from water to give the title compound (m.p. 205° C. with decomposition).

EXAMPLE 9

5-[4-(3-Carboxypropionamido)phenyl]-2(1H)-pyrazinone (a) To a stirred solution of N-phenylhydroxylamine (8 g) in ether (80 ml) at 0° C. was added dropwise over 10 minutes ethyl succinyl chloride (5.76 g). The reaction mixture was allowed to attain room temperature overnight, filtered and the filtrate evaporated to give N-(3-ethoxycarbonylpropionyl)-N-phenylhydroxylamine as an oil.

(b) N-(3-Ethoxycarbonylpropionyl)-N-phenylhydroxylamine was treated with chloropyrazine and sodium hydride in a manner similar to that described in Example 1(a) to give 5-[4-(3-ethoxycarbonylpropionamido)phenyl]-2(1H)-pyrazinone (m.p. 250° C. with decomposition).

(c) N-(3-Ethoxycarbonylpropionamido)phenyl]-2(1H)-pyrazinone (1.1 g) was heated under reflux in a mixture of methanol (20 ml) and 10% aqueous barium hydroxide solution (12 ml) for 6 hours and the solution was neutralised with dilute sulphuric acid to give the title compound (decomposes 250° C.; $\nu$(Nujol mull) 1640 (C=0), 1680 (C=0), 1710 (C=0) cm$^{-1}$).

EXAMPLE 10

5-(4-Aminophenyl)-2-(1H)-pyrazinone (a) 5-Phenyl-2-(1H)-pyrazinone (5 g) was added in portions during 30 minutes to a stirred mixture of fuming nitric acid (30 ml) and sulphuric acid (5 ml) at $-5°$ C. The mixture was stirred in the cold for 30 minutes, and the temperature of the mixture was then allowed to rise to 10° C. The mixture was then poured into ice-water (250 ml) to give 5-(4-nitrophenyl)-2(1H)-pyrazinone recrystallised from dimethylformamide, m.p. 336°-8° C., $\delta$(DMSO-d$_6$) 8.15 and 8.30 (2d, 3- and 6- protons of pyrazinone ring), 8.18 (m, phenyl); $\nu$max (Nujol mull) 3200–2500 (NH), 1690, 1675, 1545, 1510, 1349, 860 and 750 cm$^{-1}$.

(b) 5-(4-Nitrophenyl)-2-(1H)-pyrazinone (0.1 g) was hydrogenated over 10% Palladium on Charcoal (0.01 g) at atmospheric pressure in 50% aqueous dimethylformamide containing 2N sodium hydroxide (0.46 ml). Once the theoretical quantity of hydrogen uptake had been observed, the reaction mixture was filtered and the filtrate treated with HCl to pH6 and evaporated. Trituration of the residue with water afforded the title compound 0.07 g, m.p. 269°-271.5° C. (with decomposition).

(c) 5-Phenyl-2-(1H)-pyrazinone (56 g) was added in portions over 30 minutes to a stirred mixture of concentrated sulphuric acid (35 ml) and fuming nitric acid (200 ml). The temperature of the nitrating mixture was initially at $-20°$ C. and care was taken to ensure that the temperature did not rise above $-15°$ C. When the pyrazinone had completely dissolved the reaction mixture was allowed to warm to $-10°$ C., stirred for a further 30 minutes, and poured slowly on to ice/water (1500 ml). A pale yellow solid precipitated which was collected by filtration, washed with a small amount of cold water and dried to afford 5-(4-nitrophenyl)-2-(1H)-pyrazinone (58.1 g).

(d) 5-(4-Nitrophenyl)-2-(1H)-pyrazinone (4.0 g) in powder form was slurried with sodium hydroxide solution (1.47 g in water (20 ml) and ethanol (20 ml)) at room temperature. The resultant brown mixture was stirred for one hour. To this mixture were added 10% Palladium on carbon (0.4 g) slurried in water (2 ml), followed by water (8 ml) and ethanol (10 ml). The resultant mixture was hydrogenated at $3.25 \times 10^5$ Pa (45 p.s.i.) in a small Parr vessel for 30 minutes. When theoretical uptake of hydrogen had been observed, the catalyst was filtered through diatomaceous earth with water washing. The filtrate was refiltered, acidified with acetic acid to pH 4.5 and the resultant 5-(4-aminophenyl)-2-(1H)-pyrazinone (2.9 g) was collected by filtration and dried.

(e) 5-(4-Nitrophenyl)-2-(1H)-pyrazinone (0.1 g) was warmed with hydrazine hydrate (1 ml) in 50% aqueous ethanol (2.5 ml). Water (about 3 ml) was added sufficient to provide a clear solution. The mixture was allowed to cool slightly and 10% Palladium on charcoal (0.01 g) added as a slurry in a small amount of water. The well-stirred mixture was re-heated for 2 minutes, stirred without heating for 2 minutes, cooled and filtered. The filtrate was evaporated under reduced pressure to give a residue which was suspended in a little water. Dilute hydrochloric acid was added to pH6; the pale yellow solid was collected and washed with water to afford 5-(4-aminophenyl)-2-(1H)-pyrazinone (0.06 g).

(f) 5-(4-Nitrophenyl)-2-(1H)-pyrazinone (0.1 g) was warmed with water (2.5 ml) and 1N sodium hydroxide solution (0.46 ml) to about 70° C. To this solution was added 10% Palladium on charcoal (0.01 g), and subsequently hydrazine hydrate (0.1 ml). The well-stirred mixture was heated for 2 minutes, stirred for a further 2 minutes and filtered whilst hot. The filtrate was taken to pH 6 with dilute hydrochloric acid, whereupon the solid was collected by filtration, washed with water and dried to give 5-(4-aminophenyl)-2-(1H)-pyrazinone (0.07 g).

(g) In an adaptation of the process of Example 10f the filtrate was taken to pH 1–2 with dilute hydrochloric acid. To this well-stirred solution at room temperature was added sodium acetate trihydrate (1.2 g) and acetic anhydride (1 ml). The resultant mixture was stirred for 50 minutes at room temperature, the solid collected, washed with water and dried to give 5-(4-acetamidophenyl)-2(1H)-pyrazinone in 79% yield.

EXAMPLE 11

5-[4-(3-Phenylureido)phenyl]-2(1H)-pyrazinone 5-(4-Aminophenyl)pyrazin-2(1H)-one (1 g) was dissolved in dimethylformamide (25 ml) and triethylamine (0.05 ml), and the solution filtered through diatomaceous earth. Phenyl isocyanate (1 ml) was added and the dark solution was stirred for 24 hours at room temperature. The solvent was evaporated under reduced pressure to afford a residue which was washed with water. The resultant solid precipitate was collected by filtration to yield 5-[4-(3-phenylureido)phenyl]-2(1H)-pyrazinone.

EXAMPLE 12

5-(4-t-Butoxycarbonylaminophenyl)-2(1H)-pyrazinone

N-Phenyl-N-t-butoxycarbonylhydroxylamine (5.7 g) was dissolved in anhydrous dimethylformamide (50 ml) and sodium hydride (1.3 g; 50% dispersed in oil) was added to the ice-cooled, stirred solution over 30 minutes. The mixture was stirred for a further 15 minutes, chloropyrazine (2.5 ml) was added and the mixture stirred at room temperature for 3 hours. The mixture was filtered and the filtrate evaporated under reduced pressure to afford an oily residue. This was washed with petroleum ether, then worked up in glacial acetic acid, giving a yellow precipitate which was collected by filtration, dried in air and washed with chloroform. A yellow powder (2.9 g) was obtained which was recrystallised from n-propanol and dried to afford 5-(4-t-butoxycarbonylaminophenyl)-2(1H)-pyrazinone (1.5 g,) m.p. 267°–69° C.; δ(DMSO-d$_6$) 1.49 (9H, s, —C(CH$_3$)$_3$); 7.95 (d, pyr 6H); 8.08 (d, pyr 3H); νmax (Nujol mull) 1715 cm$^{-1}$, 1655 cm$^{-1}$.

EXAMPLE 13

5-[4-(3,3-Diethylureido)phenyl]-2(1H)-pyrazinone (a) 5-(4-Aminophenyl)pyrazin-2(1H)-one (1 g) was dissolved in dimethylformamide (20 ml) and triethylamine (1.0 ml). The dark solution was filtered through diatomaceous earth, and then added dropwise to an ice-cooled solution of N,N'-carbonyldiimidazole (3.0 g) in dimethylformamide (20 ml) over 1½ hours The mixture was stirred for a further 30 minutes, to form 5-[4-(isocyanato)phenyl]-2(1H)-pyrazinone.

(b) Diethylamine (4.0 ml) was added, and the resultant mixture was stirred at room temperature for 45 minutes, and evaporated under reduced pressure to afford a dark oil. Water was added, and the resultant brown solid precipitate collected by filtration, washed with more water and dried to afford a solid (0.9 g). This was dissolved in n-propanol and filtered through diatomaceous earth. The filtrate was evaporated under reduced pressure and the residue washed with water. The solid was collected by filtration, washed with water and dried to yield 5-[4-(3,3-diethylureido)phenyl]-2(1H)-pyrazinone, (0.7 g), m.p. 154°–55° C.

EXAMPLE 14

5-(4-Isonicotinamidophenyl)-2(1H)-pyrazinone

To a stirred solution of 5-(4-aminophenyl)-2-(1H)-pyrazinone hydrobromide (1.3 g) in dimethylformamide (20 ml) containing pyridine (1 ml) was added a solution of isonicotinyl chloride hydrochloride (1.3 g) in dimethylformamide (10 ml). The mixture was heated under reflux for 4 hours and evaporated to small volume. Water was added to the residue and the solid (1.0 g) was collected, washed with water, dilute sodium hydroxide solution (pH8), water and then dried to give the title compound m.p. 303°–308° C.

EXAMPLE 15

5-(4-Ureidophenyl)-2(1H)-pyrazinone 5-(4-Aminophenyl)-2(1H)-pyrazinone hydrochloride (1.0 g) was dissolved in water (25 ml), to which solution potassium cyanate (0.4 g) and 4-dimethylaminopyridine (about 0.005 g) were added. The mixture was stirred at room temperature for 18 hours and the resulting suspended material collected by filtration. This was washed in hot dimethylformamide (30 ml), the insoluble material being collected and washed with water to afford the title compound, m.p.>300° C.; n.m.r. δ(DMSO-d$_6$) 5.90 (s, 2H,—CONH$_2$), 7.98, 8.10 (2d, 2H, pyridine H's); ν(liquid paraffin) 1710, 1665 cm$^{-1}$.

EXAMPLE 16

5-[4-(3-Methylureido)phenyl]-2(1H)-pyrazinone 5-(4-Aminophenyl)-2(1H)-pyrazinone hydrochloride (1.0 g) was suspended in dimethylformamide (30 ml) and triethylamine (1.2 ml) was added. The dark solution was filtered. Methyl isocyanate (0.53 ml) was added and the mixture was stirred for 17 hours at room temperature. The mixture was evaporated to dryness and the black residue washed with water; the insoluble material was collected by filtration and then reprecipitated from dimethylformamide solution with water. The precipitate was filtered off and the filtrate evaporated to dryness. The cream-coloured residue was collected to afford the title compound, m.p.>300° C.; C$_{12}$H$_{12}$N$_4$O$_2$ Calculated: C 59.01; H 4.95; N 22.94: Found: C 59.09; H 4.94; N 22.90: νmax (liquid paraffin) 1675, 1642 cm$^{-1}$; N.m.r. δ(DMSO-d$_6$) 2.76 (d, 3H, CH$_3$), 5.98 (q, 1H, —NHCH$_3$), 7.91, 8.08 (2d, 2H, pyridine H's).

EXAMPLE 17

5-[4-(3-Ethylureido)phenyl]-2(1H)-pyrazinone 5-(4-Aminophenyl)-2(1H)-pyrazinone hydrochloride (1.5 g) was suspended in dimethylformamide (20 ml) and triethylamine (3 ml) was added. The dark solution was filtered. Ethyl isocyanate (0.53 ml) was prepared by slowly adding lead tetra acetate (7.3 g) to a solution of propionamide (1.2 g) in dimethylformamide (50 ml). The solution was initially blood-red, but after stirring for one hour at room temperature it turned colourless. The solution of pyrazinone was added and the mixture stirred at room temperature for 36 hours. It was evaporated to dryness and the residue was washed with water; the resulting orange solid was collected by filtration. Recrystallization from glacial acetic acid afforded the title compound; m.p.>300° C.; νmax (liquid paraffin) 1660, 1640 cm$^{-1}$; δ(DMSO-d$_6$) 1.07 (t, 3H, CH$_3$), 6.05 (t, 1H, —NHEt), 7.93, 8.08 (2d, 2H, pyridine H's).

EXAMPLE 18

5-[4-(3-t-Butylureido)phenyl]-2(1H)-pyrazinone 5-(4-Aminophenyl)-2(1H)-pyrazinone hydrochloride (1.5 g) was suspended in dimethylformamide (25 ml) and triethylamine (1.0 ml) was added. The dark solution was filtered. t-Butyl isocyanate (2.5 ml) was added to the filtrate. After 13 days at room temperature the solution was evaporated and the residue washed with water. The solid material was collected by filtration, then reprecipitated from dimethylformamide solution with water. The title compound was collected as a buff solid, m.p.>300° C.; n.m.r. δ(DMSO-d$_6$) 1.30 (s,9H, Bu), 7.98, 8.09 (2d, 2H, pyridine H's), i.r. ν(liquid paraffin) 1690, 1645 cm$^{-1}$.

EXAMPLE 19

5-[4-(4-Ethoxycarbonylaminophenyl]-2(1H)-pyrazinone (a) N-Phenylhydroxylamine

Nitrobenzene (100 g) was added to a solution of ammonium chloride (25 g) in water (1600 ml). The mixture was heated to 55° C. and zinc dust (116 g) added over a period of 45 minutes, maintaining the temperature during this addition between 65°–70° C. The mixture was vigorously stirred for a further 45 minutes at 65°–70° C., filtered whilst hot through diatomaceous earth and the filtrate was allowed to cool whereupon an emulsion formed. This emulsion was saturated with sodium chloride to form yellow needle-shaped crystals which were collected by filtration to afford N-phenylhydroxylamine (67 g), m.p. 65°–67° C. This material was unstable.

(b) Ethyl N-hydroxy-N-phenylcarbamate

N-Phenyl hydroxylamine (67 g) was dissolved in diethyl ether (600 ml), dried over MgSO$_4$ and filtered. The solution was cooled and stirred, and to this was added over 30 minutes ethyl chloroformate (30 g). The solution was stirred for a further 2 hours. The white solid was filtered off and washed with diethylether (2×100 ml). The filtrate and washings were combined, washed with water (2×150 ml), dried over MgSO$_4$, filtered and evaporated under reduced pressure to afford an oil. This oil was purified on a silica column using chloroform as eluant, to afford ethyl N-hydroxy-N-phenyl carbamate (21 g) as an oil.

(c) 5-(4-Ethoxycarbonylaminophenyl)-2(1H)-pyrazinone

Ethyl N-hydroxy-N-phenylcarbamate (7.9 g) was added to a solution of potassium hydroxide (2.45 g) in ethanol (125 ml). After the solution had been stirred for 30 minutes, chloropyrazine (5 g) and a small amount of molecular sieve (4A) pellets were added. The solution was stirred for two hours and allowed to stand for 144 hours to give a dark brown solution. This solution was evaporated under reduced pressure to give an oil which was washed with dilute acetic acid and solidified. This solid was recrystallised from n-propanol, stirred with water for two hours to remove salts, collected and dried to afford the title compound (1.8 g), m.p. 260°–262° C.

EXAMPLE 20

A solution of 5-(4-benzyloxycarbonylaminophenyl)-2(1H)-pyrazinone (1.1 g) in 15% w/v hydrogen bromide in acetic acid solution (30 ml) was refluxed for 30 min. The yellow precipitate which formed was filtered off and it was washed with a little 1-propanol and then recrystallised from ethanol-water containing 2 drops of concentrated hydrobromic acid to give 5-(4-aminophenyl)-2(1H)-pyrazinone hydrobromide (1.03 g m.p.>300° C.).

EXAMPLE 21

5-[4-(3-(2-Acetamidoethyl)ureido)phenyl]-2(1H)-pyrazinone

In a manner similar to Example 13b, 5-[4-(isocyanato)phenyl]-2(1H)-pyrazinone is reacted with 2-acetamidoethylamine (1 g) in dimethylformamide (5 ml) for 17 hours at room temperature to form the title compound, m.p. 238°–44° C.; δ(DMSO-d$_6$) 1.80 (s, 3H, COC$\underline{H}_3$), 7.94, 8.08 (2s, 2H, pyrazinone H's).

EXAMPLE 22

5-[4-(3-(2-Aminoethyl)ureido)phenyl]-2(1H)-pyrazinone

5-[4-(3-(2-Acetamidoethyl)ureido)phenyl]-2(1H)-pyrazinone was hydrolysed by heating with hydrochloric acid to form the title compound, as the hydrochloride; δ(D$_2$O/DCl) 3.15, 3.45 (2t, 4H, —C$\underline{H}_2$C$\underline{H}_2$—), 7.81, 8.08 (2d, pyrazinone H's).

EXAMPLE 23

5-[4-(3-(2-Hydroxyethyl)ureido)phenyl]-2(1H)-pyrazinone

In a manner similar to Example 13b, 5-[4-(isocyanato)phenyl]-2(1H)-pyrazinone was reacted with 2-hydroxyethylamine (0.5 g) in dimethylformamide (5 ml) for 17 hours at room temperature. The mixture was purified by flash chromatography (chloroform—20% methanol/80% chloroform); the desired fractions were combined and evaporated under reduced pressure to afford a residue. This residue was washed with chloroform and dried to form the title compound; δ(DMSO-d$_6$) 3.17 (sextet, 2H, —NHC$\underline{H}_2$), 3.47 (t, 2H, —C$\underline{H}_2$OH), 7.94, 8.06 (2d, J=1 Hz, pyrazinone H's).

EXAMPLE 24

5-[4-(3-(4-Methylpiperazino)ureido)phenyl]-2(1H)-pyrazinone

In a manner similar to Example 13b, 5-[4-(isocyanato)phenyl]-2(1H)-pyrazinone is reacted with 4-methylpiperazine to form the title compound.

EXAMPLE 25

Using a procedure similar to that of Example 17 p-tolyl isocyanate is reacted with 5-(4-aminophenyl)-2(1H)-pyrazinone (or its hydrobromide salt) to give 5-[4-(3-p-tolylureido)phenyl]-2(1H)-pyrazinone.

EXAMPLE 26

(a) 5-(4-Aminophenyl)-2(1H)-pyrazinone hydrobromide is treated with dimethyl carbamoyl chloride using a procedure similar to that of Example 5 to form 5-[4-(3,3-dimethylureido)phenyl]-2(1H)-pyrazinone.

(b) 5-(4-Aminophenyl)-2(1H)-pyrazinone (0.25 g) was dissolved in a solution of triethylamine (0.25 ml) in dimethylformamide (10 ml). This was filtered and added dropwise over 30 minutes to an ice-cooled solution of N,N'-carbonyldi-imidazole. The mixture was stirred for a further 30 minutes at 0° C.

To this mixture was added a filtered solution of triethylamine (1.7 ml) in dimethylformamide (5 ml). The mixture was stirred for a further 17 hours at room temperature, and evaporated under reduced pressure to afford a dark oil. This oil was dissolved in chloroform and placed on a short silica column (chloroform—20% methanol/80% chloroform). The desired fractions were combined, evaporated under reduced pressure, washed with chloroform and dried to afford 5-[4-(3,3-dimethylureido)phenyl]-2(1H)-pyrazinone; m.p. 256°–60° C.; δ(DMSO-d$_6$) 2.93 (s, 6H, —N(CH$_3$)$_2$), 7.97, 8.09 (2 broad s, 2H, pyrazinone H's).

EXAMPLE 27

| Ingredients | Amounts |
|---|---|
| 5-(4-Acetylaminophenyl)-2(1H)—pyrazinone | 100 mg |
| Sucrose | 40 mg |
| Starch | 15 mg |
| Talc | 3 mg |
| Stearic acid | 1 mg |

The ingredients are screened, mixed and filled into a hard gelatin capsule. Such capsules are administered orally from 1 to 4 times daily to a patient in need of improved cardiac function.

EXAMPLE 28

| Ingredients | Amounts |
|---|---|
| 5-(4-Aminophenyl)-2(1H)—pyrazinone | 100 mg |
| Sucrose | 40 mg |
| Starch | 15 mg |
| Talc | 3 mg |

| Ingredients | Amounts |
|---|---|
| Stearic acid | 1 mg |

The ingredients are screened, mixed and filled into a hard gelatin capsule. Such capsules are administered orally from 1 to 4 times daily to a patient in need of improved cardiac function.

EXAMPLE 29

| Ingredients (for slow intravenous injection) | Amounts % w/vol |
|---|---|
| 5-(4-Acetylaminophenyl)-2(1H)—pyrazinone | 0.1 |
| Sodium chloride | 0.9 |
| Sodium hydroxide sufficient to give a pH of about | 9.5 |
| Water for injection (E.P.) up to | 100% |

The ingredients are mixed to give a total volume, for example of about 7 to 10 ml, which is filled into a vial, sealed and sterilised.

EXAMPLE 30

5-(4-Isobutyramidophenyl)-2(1H)-pyrazinone

In a procedure analogous to Example 3(a) 5-(4-aminophenyl)-2(1H)-pyrazinone hydrobromide and isobutyric anhydride were reacted to give, after recrystallisation from glacial acetic acid, the title compound; m.p. 279.5°–280° C.: δ(DMSO-$d_6$) 1.03 (d, J=8 Hz, 6H, —CH(CH$_3$)$_2$), 3.58 (q,J=8 Hz, 1H), 7.98, 8.08 (2d, 2H, pyrazinone H's).

EXAMPLE 31

5-(4-Propionamidophenyl)-2-(1H)-pyrazinone

In a procedure analogous to Example 3(a) 5-(4-aminophenyl)-2(1H)-pyrazinone hydrobromide and propionic anhydride were reacted to give, after recrystallisation from glacial propionic acid, the title compound; m.p. 270°–272° C.: δ(DMSO-$d_6$) 1.1 (t, CH$_2$), 2.33 (q, CH$_3$), 7.97, 8.08 (2d, 2H, pyrazinone H's).

What we claim is:

1. A compound of the formula (I):

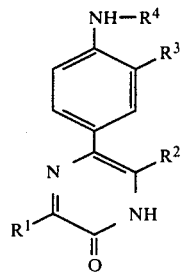

or a pharmaceutically acceptable salt thereof, wherein $R^1$, $R^2$ and $R^3$ are independently hydrogen or $C_{1-4}$ alkyl, and $R^4$ is hydrogen; or $R^4$ is a $C_{1-6}$ alkoxycarbonyl group optionally substituted by amino, hydroxy, $C_{1-4}$ alkoxy or carboxy (wherein the substituent is not on the carbon atom adjacent to the —CO—O— moiety); or $R^4$ is a group —CO—(NR$^5$)$_n$-R$^6$ wherein n is zero or one, $R^6$ is hydrogen; or $R^6$ is optionally substituted $C_{1-6}$ alkyl wherein the optional substituent is up to three groups or atoms selected from carboxy, chloro, bromo, fluoro, amino, hydroxy, $C_{1-4}$ alkoxy, $C_{1-6}$ alkanoylamino, phenyl and phenyl substituted with amino, chloro, fluoro, bromo or $C_{1-4}$ alkyl; or $R^6$ is optionally substituted phenyl wherein the optional substitutent is amino, chloro, fluoro, bromo, $C_{1-4}$ alkyl or $C_{1-4}$ alkoxy; or $R^6$ is optionally substituted pyridyl wherein the optional substituent is amino, hydroxy, $C_{1-4}$ alkyl or $C_{1-4}$ alkoxy, and $R_5$ is hydrogen or $C_{1-6}$ alkyl or $R^5$ and $R^6$ form together with the nitrogen atom to which they are attached a piperidine, morpholino, piperazine or N-($C_{1-6}$) alkylpiperazine ring; with the exception of 5-(4-aminophenyl)-2-(1H)-pyrazinone.

2. A compound according to claim 1 wherein $R^4$ is hydrogen or a group —CO(NR$^5$)$_n$—R$^6$ wherein $R^5$, $R^6$ and n are as defined in claim 1, with the proviso that when $R^5$ and $R^6$ form, together with the nitrogen atom to which they are attached, a ring system it is piperidino, piperazine or N-($C_{1-6}$)alkylpiperazine.

3. A compound according to claim 1 with the proviso that $R^4$ is not hydrogen.

4. A compound according to claim 1 wherein $R^1$, $R^2$ and $R^3$ are simultaneously hydrogen.

5. A compound according to claim 1 wherein $R^4$ is $C_{1-6}$ alkanoyl.

6. A compound according to claim 5 wherein $R^4$ is acetyl.

7. A compound according to claim 1 wherein $R^4$ is $C_{1-6}$ alkoxycarbonyl.

8. A compound according claim 1 wherein $R^4$ is $C_{1-6}$ alkylaminocarbonyl.

9. A compound according to claim 1 which is:
5-(4-aminophenyl)-3-methyl-2(1H)-pyrazinone,
5-(4-aminophenyl)-6-methyl-2(1H)-pyrazinone,
5-(4-acetamidophenyl)-2(1H)-pyrazinone,
5-(4-acetamidophenyl)-3-methyl-2(1H)-pyrazinone,
5-(4-benzamidophenyl)-2(1H)-pyrazinone,
5-[4-(4-aminobenzamido)phenyl]-2(1H)-pyrazinone,
5-[4-(3-aminobenzamido)phenyl]-2(1H)-pyrazinone,
5-[4-(5-chloro-n-valeramido)phenyl]-2(1H)-pyrazinone,
5-[4-(3-carboxypropionamido)phenyl]-2(1H)-pyrazinone,
5-[4-(3-ethylureido)phenyl]-2(1H)-pyrazinone,
5-[4-(3-phenylureido)phenyl]-2(1H)-pyrazinone,
5-[4-(3-p-tolylureido)phenyl]-2(1H)-pyrazinone,
5-[4-(3,3-dimethylureido)phenyl]-2(1H)-pyrazinone,
5-(4-(3,3-diethylureido)phenyl]-2(1H)-pyrazinone,
5-(4-isonicotinamidophenyl)-2-(1H)-pyrazinone,
5-(4-ureidophenyl)-2(1H)-pyrazinone,
5-[4-(3-methylureido)phenyl]-2(1H)-pyrazinone,
5-[4-(3-t-butylureido)phenyl]-2(1H)-pyrazinone, or
5-[4-(4-ethoxycarbonylaminophenyl]-2(1H)-pyrazinone,
5-(4-t-butoxycarbonylaminophenyl)-2(1H)-pyrazinone,
5-[4-(3-(2-acetamidoethyl)ureido)phenyl]-2(1H)-pyrazinone,
5-[4-(3-(2-aminoethyl)ureido)phenyl]-2(1H)-pyrazinone,
5-[4-(3-(2-hydroxyethyl)ureido)phenyl]-2(1H)-pyrazinone,
5-[4-(3-(4-methylpiperazino)ureido)phenyl]-2(1H)-pyrazinone,
5-(4-isobutyramidophenyl)-2(1H)-pyrazinone,
5-(4-propionamidophenyl)-2(1H)-pyrazinone;
or a pharmaceutically acceptable salt thereof.

10. 5-(4-Acetamidophenyl)-2-(1H)-pyrazinone.

* * * * *

UNITED STATES PATENT AND TRADEMARK OFFICE
CERTIFICATE OF CORRECTION

PATENT NO. : 4,556,711
DATED : December 3, 1985
INVENTOR(S) : John C. Emmett et al.

It is certified that error appears in the above-identified patent and that said Letters Patent is hereby corrected as shown below:

On the title page item (73) should read

-- /73/ Assignee: Smith Kline & French Laboratories Ltd., Welwyn Garden City, England --.

Signed and Sealed this

Twenty-ninth Day of April 1986

[SEAL]

Attest:

DONALD J. QUIGG

Attesting Officer    Commissioner of Patents and Trademarks